US009332731B2

(12) United States Patent
Komatsubara et al.

(10) Patent No.: US 9,332,731 B2
(45) Date of Patent: May 10, 2016

(54) PET DIAPER

(75) Inventors: Daisuke Komatsubara, Kagawa (JP);
Takeshi Ikegami, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 17 days.

(21) Appl. No.: 14/008,282

(22) PCT Filed: Mar. 13, 2012

(86) PCT No.: PCT/JP2012/056468
§ 371 (c)(1),
(2), (4) Date: Dec. 4, 2013

(87) PCT Pub. No.: WO2012/132886
PCT Pub. Date: Oct. 4, 2012

(65) Prior Publication Data
US 2014/0076246 A1  Mar. 20, 2014

(30) Foreign Application Priority Data
Mar. 29, 2011  (JP) .................................. 2011-073663

(51) Int. Cl.
*A01K 23/00* (2006.01)
*A61F 13/49* (2006.01)
*A61F 13/15* (2006.01)

(52) U.S. Cl.
CPC ................. *A01K 23/00* (2013.01); *A61F 13/15* (2013.01); *A61F 13/49* (2013.01); *A61F 2013/15186* (2013.01)

(58) Field of Classification Search
CPC ....... A01K 23/00; A61F 5/4401; A61F 13/49; A61F 13/49014

USPC ........... 119/867–69, 167, 169, 170; 604/358, 604/358.03, 385.23, 385.24, 391, 394
IPC .......................... A01K 23/00; A61F 5/44,13/49
See application file for complete search history.

(56) References Cited

U.S. PATENT DOCUMENTS 5,383,867 A * 1/1995 Klinger .................... 604/385.23
5,954,015 A * 9/1999 Ohta ............................ 119/850
(Continued)

FOREIGN PATENT DOCUMENTS

JP         3031321 U    9/1996
JP         1075679 A    3/1998
(Continued)

OTHER PUBLICATIONS

English-language translation of JP 2012-183045.*
Corresponding International Application No. PCT/JP2012/056468 Search Report dated May 15, 2012.

*Primary Examiner* — Lisa Tsang
(74) *Attorney, Agent, or Firm* — Hauptman Ham, LLP

(57) ABSTRACT

A pet diaper is equipped with a front surface layer, a back surface layer, and an absorbent layer disposed between the front surface layer and the back surface layer. The pet diaper has a back portion, an abdominal portion, and a crotch portion disposed between the back portion and the abdominal portion. The pet diaper is further equipped with: a first cut portion that is provided on the back portion and that is formed as a convex curve rounding towards the end portion of the back portion; a second cut portion that is provided closer to the crotch portion than the first cut portion and that is formed as a convex curve rounding towards the end portion of the back portion; and a first perforated portion that is formed so as to extend from the second cut portion towards the first cut portion.

15 Claims, 9 Drawing Sheets

(56) References Cited

U.S. PATENT DOCUMENTS

| | | | |
|---|---|---|---|
| 7,195,618 B2* | 3/2007 | Ikegami | 604/351 |
| 7,635,360 B2* | 12/2009 | Van Gompel et al. | 604/385.19 |
| 2006/0217678 A1* | 9/2006 | Ikegami et al. | 604/386 |
| 2007/0149941 A1* | 6/2007 | Ikegami et al. | 604/385.09 |
| 2008/0125735 A1* | 5/2008 | Busam et al. | 604/367 |
| 2012/0067298 A1* | 3/2012 | Rich | 119/856 |

FOREIGN PATENT DOCUMENTS

| | | | |
|---|---|---|---|
| JP | 2003047360 A | | 2/2003 |
| JP | 2012183045 A | * | 9/2012 |

* cited by examiner

PET DIAPER

RELATED APPLICATIONS

The present application is based on and claims priority from International Application Number PCT/JP2012/056468, filed Mar. 13, 2012, and Japanese Application Number 2011-073663, filed Mar. 29, 2011, the disclosure of which is hereby incorporated by reference herein in its entirety.

TECHNICAL FIELD

The present invention relates to a pet diaper to be put on a pet such as a dog or a cat.

BACKGROUND ART

Heretofore, a pet diaper used for a pet such as a dog or a cat has been proposed. Such a pet diaper includes: a back portion disposed in a vicinity of a back of a pet wearing the diaper; an abdominal portion disposed in a vicinity of an abdomen of the pet; and a crotch portion disposed in a vicinity of a crotch (between bases of hind legs) of the pet, in which a liquid absorbent is disposed in the abdominal portion and the crotch portion.

Another pet diaper has been proposed, which can be preferably put on a pet having a tail, by providing a tail through-hole for passing the tail through the back portion.

For example, Patent Document 1 proposes a pet diaper, in which a tail through-hole is formed by perforations, and the tail through-hole is configured to include an annular portion and a division portion dividing the annular portion.

According to the pet diaper proposed in Patent Document 1, perforations constituting the annular portion and the division portion are appropriately incised in accordance with the size and position of the tail of the diaper-wearing pet, and the tail is passed through the incised portion; as a result, a tail through-hole can be formed in accordance with the size and position of the tail of the diaper-wearing pet.

Patent Document 1: Japanese Unexamined Patent Application Publication No. H10-75679

DISCLOSURE OF THE INVENTION

Problems to be Solved by the Invention

It may be noted that a position of a urethral opening of a pet such as a dog or a cat is different depending on the gender. In other words, a urethral opening of a female pet is located between bases of hind legs, whereas a urethral opening of a male pet is located on a genital tip anterior to bases of hind legs. Therefore, even in a case in which a pet diaper is put on a pet of the same kind and/or size, if the pet diaper is put on a male pet, in order to preferably absorb urine excreted from a part anterior to the bases of the hind legs, it is preferable for the abdominal portion including the absorbent body to be positioned anteriorly to the body as much as possible. On the other hand, in a case in which the pet diaper is put on a female pet, in order to preferably absorb urine excreted from a part between the bases of the hind legs, it is preferable for the crotch portion including the absorbent body to be positioned posteriorly to the body (to the vicinity of the tail) as much as possible.

In this regard, the pet diaper proposed in Patent Document 1 can form a tail through-hole in a desired position in the annular portion in accordance with the size and position of the tail. However, in this pet diaper, a tail through-hole can be formed by incising any position of the annular portion and the division portion; therefore, from the perspective of disposing an absorbent in an appropriate position of the pet, it has been difficult to form a tail through-hole in a preferred position in accordance with the gender of the pet. As a result, the pet diaper has not been able to be fit in an appropriate position in accordance with the gender of the pet in some cases.

Therefore, an object of the present invention is to provide a pet diaper which can be fit in an appropriate position of a pet in accordance with the gender of the pet.

Means for Solving the Problems

The present invention relates to a pet diaper including a liquid permeable surface layer; a liquid impermeable back layer; a liquid absorbent layer disposed between the surface layer and the back layer, a back portion disposed in a vicinity of a back of a pet; an abdominal portion disposed in a vicinity of an abdomen of the pet; a crotch portion disposed in a vicinity of a crotch of the pet, the crotch portion disposed between the back portion and the abdominal portion; a first cut portion provided in the back portion, and formed as a convex opposite to the crotch portion or as a convex toward the crotch portion; a second cut portion provided closer to the crotch portion than the first cut portion, and formed as a convex opposite to the crotch portion or as a convex toward the crotch portion; and a first easily-incised portion formed to extend from the second cut portion toward the first cut portion.

The first cut portion and/or the second cut portion are/is preferably configured to include a plurality of incised portions and a non-incised portion provided between two of the incised portions that are adjacent to each other.

It is preferable for the first easily-incised portion to be configured by perforations, and a length of the incised portions to be configured to be longer than a length of the perforations.

The pet diaper preferably further includes a second easily-incised portion extending from the first cut portion to an end side of the back portion.

The absorbent layer is preferably configured to include a liquid absorbent core and a core wrapping sheet wrapping the absorbent core, the absorbent core is disposed in the abdominal portion and the crotch portion, and the core wrapping sheet is disposed in the abdominal portion, the crotch portion and the back portion.

Effects of the Invention

According to the pet diaper of the present invention, the pet diaper can be put on a pet in an appropriate position in accordance with the gender of the pet.

Figure 1:
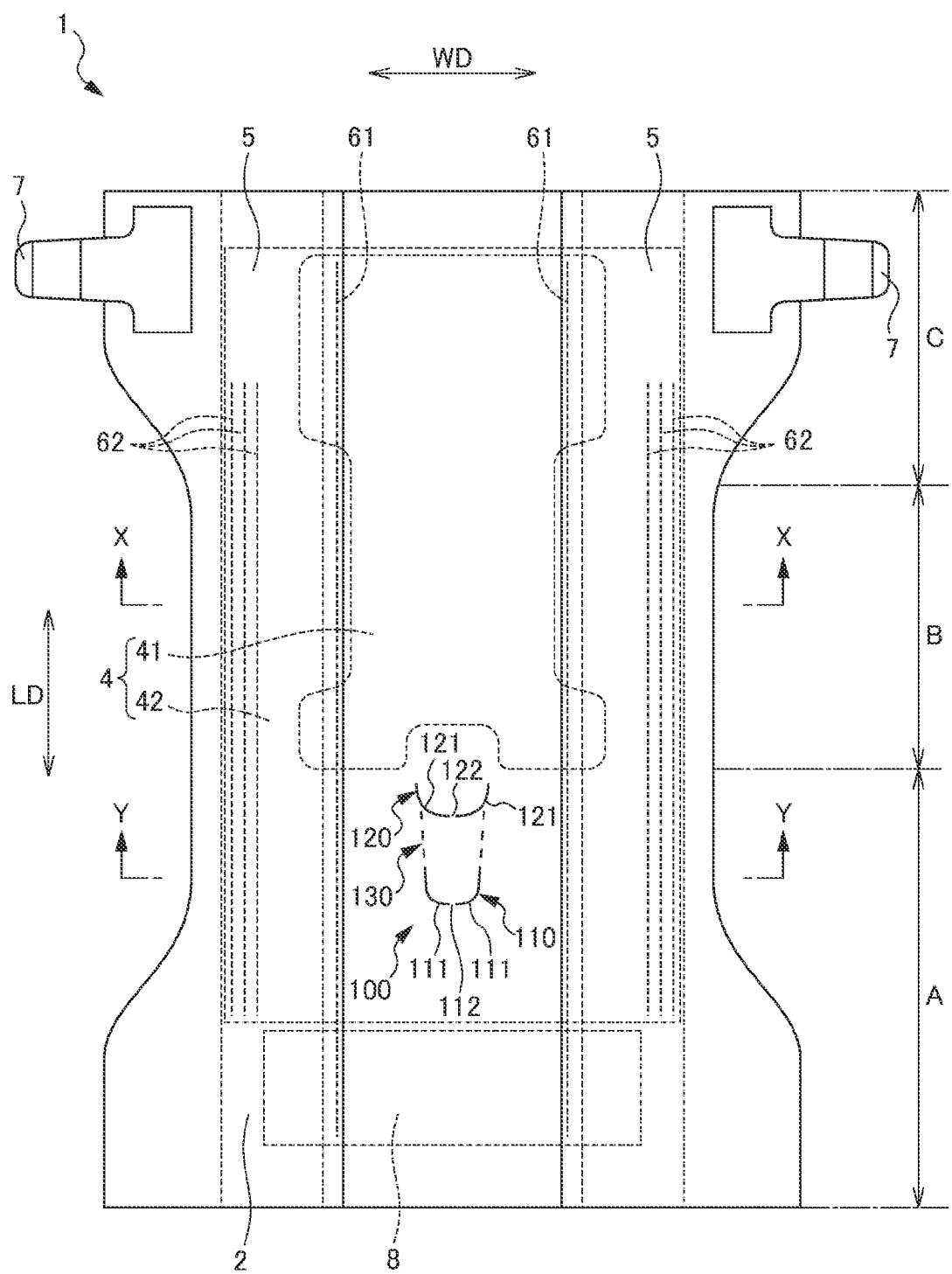
FIG. 1 is a plan view showing a pet diaper according to a first embodiment of the present invention.

EXPLANATION OF REFERENCE NUMERALS 1 pet diaper
2 surface sheet (surface layer)
3 back layer
4 absorbent body (absorbent layer)
41 absorbent core
42 core wrapping sheet
110 the first cut portion
111 incised portion
112 non-incised portion
120 second cut portion
121 incised portion
122 non-incised portion
130 first easily-incised portion
140 second easily-incised portion
A back portion
B crotch portion
C abdominal portion

PREFERRED MODE FOR CARRYING OUT THE INVENTION

Preferred embodiments of the pet diaper according to the present invention are hereinafter described with reference to the drawings.

First of all, a pet diaper of a first embodiment is described with reference to FIGS. 1 to 4.

As shown in FIG. 1, a pet diaper 1 of the first embodiment is configured to be elongated in a plan view, and has a shape whose central portion in a longitudinal direction is constricted inwardly in a width direction. The pet diaper 1 includes: a back portion A disposed on one end side in the longitudinal direction; an abdominal portion C disposed on another end side in the longitudinal direction; and a crotch portion B disposed between the back portion A and the abdominal portion C, and a tail through-hole portion 100 is formed for passing a pet tail through in the back portion A. The tail through-hole portion 100 will be described later in detail.

In the present embodiment, the back portion A refers to an area disposed in the vicinity of the back (a region including the back and the tail) of a diaper-wearing pet. The abdominal portion C refers to an area disposed in the vicinity of the abdomen of the diaper-wearing pet. The crotch portion B refers to an area disposed in the vicinity of the crotch (between the bases of the hind legs, including the vicinity of the bases) of the diaper-wearing pet.

Figure 2:
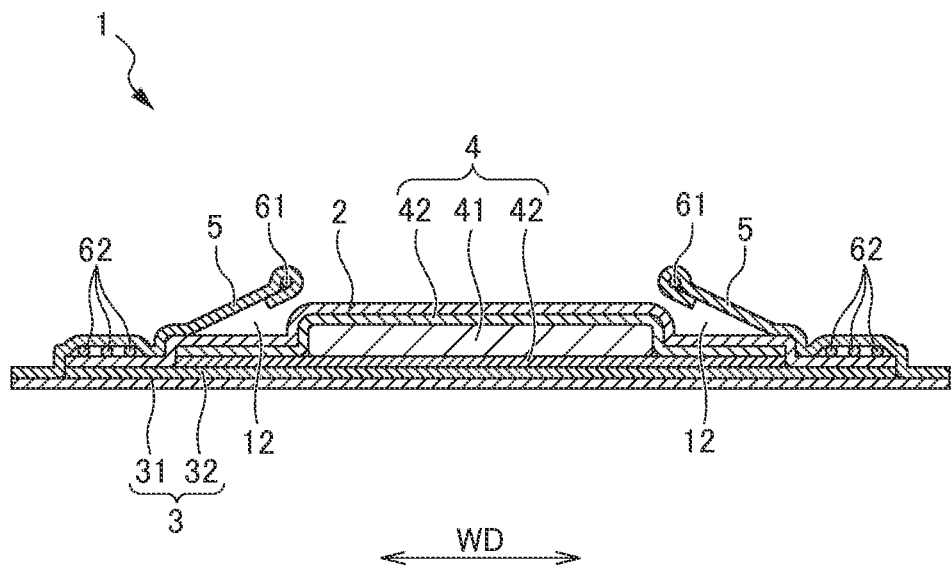
FIG. 2 is a cross-sectional view taken along a line X-X in FIG. 1.
Figure 3:
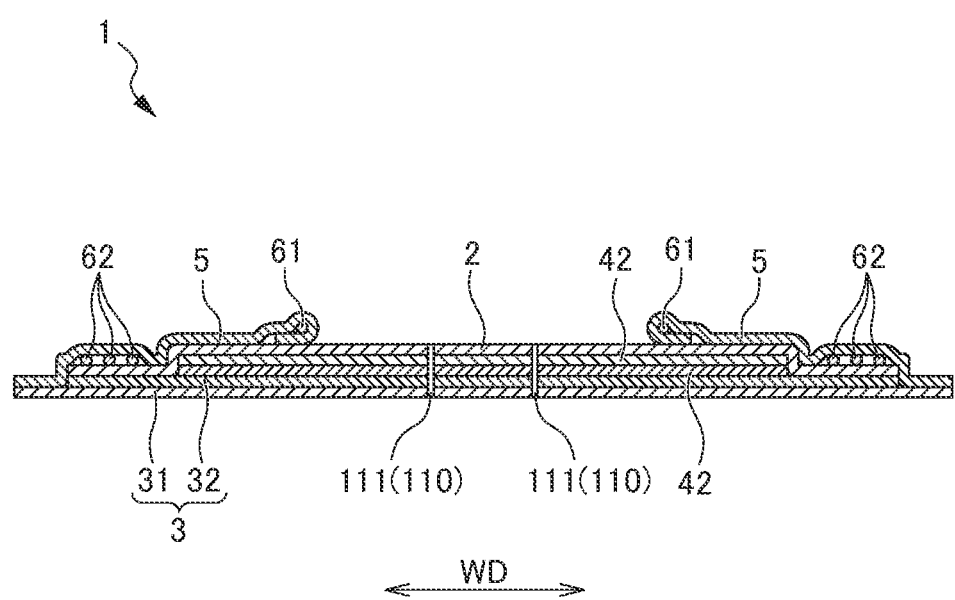
FIG. 3 is a cross-sectional view taken along a line Y-Y in FIG. 1.

As shown in FIGS. 1 to 3, the pet diaper 1 includes a surface sheet 2 as a surface layer, a back sheet 31 and a waterproof sheet 32 both constituting a back layer 3, an absorbent body 4 as an absorbent layer, a pair of side sheets 5 disposed on an outer face side of the surface sheet 2, a pair of first elastic members 61, a pair of second elastic members 62, a pair of fastening tapes 7, and a landing tape 8.

As shown in FIG. 1, the surface sheet 2 is configured in a rectangular shape. The surface sheet 2 mainly constitutes a surface on a side abutting on a body of the diaper-wearing pet. Nonwoven fabric with or without pores, or porous plastic sheets can be used as the surface sheet 2.

As shown in FIGS. 1 to 3, the back sheet 31 is configured in a rectangular shape, being wider than the surface sheet 2, and having a length substantially equal to the surface sheet 2. The back sheet 31 has a shape that coincides with an external shape of the pet diaper 1. The back sheet 31 constitutes a surface of the pet diaper 1, the surface being opposite to the pet body side.

As shown in FIGS. 2 and 3, the waterproof sheet 32 is configured to be wider than the surface sheet 2 and narrower than the back sheet 31. The waterproof sheet 32 is disposed on a surface on the surface sheet 2 side of the back sheet 31.

Hydrophobic nonwoven fabric, an impermeable plastic film, a laminated sheet made of a nonwoven fabric and an impermeable plastic film, SMS nonwoven fabric that sandwiches highly water-resisting meltblown nonwoven fabric with strong spun-bonded nonwoven fabric, or the like can be used as the back sheet 31 and the waterproof sheet 32.

The surface sheet 2, the back sheet 31 and the waterproof sheet 32 are disposed across the back portion A through the abdominal portion C of the pet diaper 1.

Figure 4:
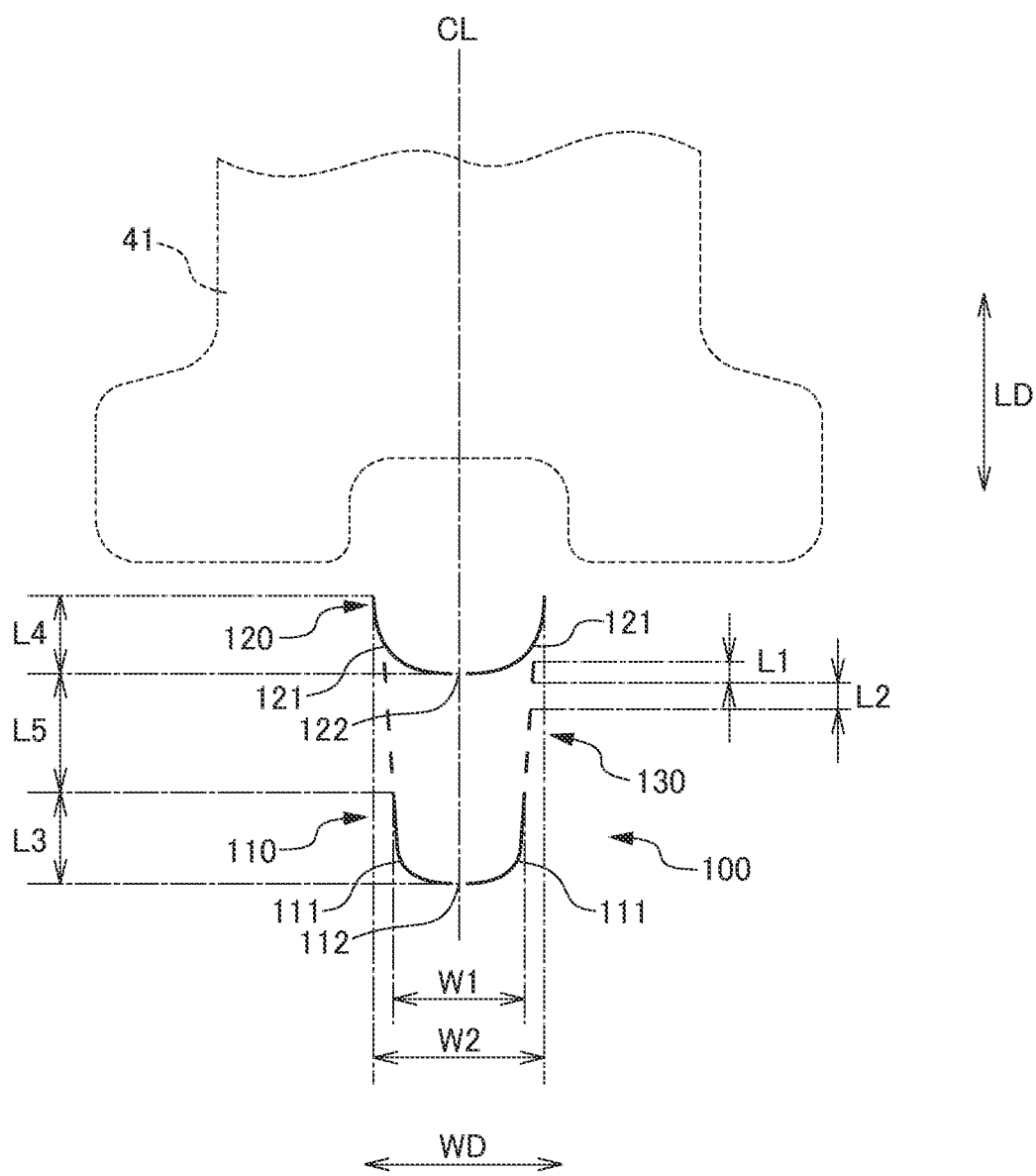
FIG. 4 is an enlarged plan view showing a tail through-hole portion according to the first embodiment.

As shown in FIG. 4, the absorbent body 4 is disposed to intervene between the surface sheet 2 and the back layer 3 which are laminated together. As shown in FIGS. 1 to 3, the absorbent body 4 includes a liquid retentive absorbent core 41, and a core wrapping sheet 42 that wraps the absorbent core 41.

As shown in FIG. 1, the absorbent core 41 is configured in a substantially rectangular shape, and is disposed in the abdominal portion C and the crotch portion B. More specifically, the absorbent core 41 has a shape, in which a pair of side portions corresponding to the crotch portion B is constricted inwardly in the width direction of the pet diaper 1, and a central portion at the end on the back portion A side is concaved.

The core wrapping sheet 42 wraps the absorbent core 41 by being disposed on both of the surface sheet 2 side and the back layer 3 side of the absorbent core 41. As shown in FIG. 1, the core wrapping sheet 42 is configured in a rectangular shape larger than the absorbent core 41, and is disposed in the abdominal portion C, the crotch portion B and the back portion A.

In other words, in the first embodiment, the absorbent core 41 is not disposed in the back portion A, but only the core wrapping sheet 42 is disposed in the back portion A.

Fluff pulp that retains high absorbent polymer can be used as the absorbent core 41. Examples of the fluff pulp used as the absorbent core 41 include chemical pulp, cellulose fibers, and artificial cellulose fibers such as rayon and acetate. Examples of the high absorbent polymer include starch-, acrylic acid-, and amino acid-based granular or fibrous polymers.

A liquid permeable sheet such as tissue, nonwoven fabric, or an apertured film can be used as the core wrapping sheet 42.

As shown in FIG. 1, the pair of side sheets 5 is configured in an elongated rectangular shape, and is disposed on the body side of the side portions along the longitudinal direction of the surface sheet 2. The length of the pair of side sheets 5 is configured to be substantially equal to the length of the surface sheet 2 and the back sheet 31. As shown in FIGS. 2 and 3, outer edges of the pair of side sheets 5 coincide with positions of the sides of the back sheet 31. Outer edges of the pair of side sheets 5 are joined to the side portions of the back sheet 31.

Inner edges of the pair of side sheets 5 are free ends at least in the central portion of the pet diaper 1 in the longitudinal direction.

A water-repellant or hydrophobic material is preferably used for the side sheet 5; and more specifically, various non-woven fabric such as spun lace nonwoven fabric, spunbond nonwoven fabric, thermobonded nonwoven fabric, meltblown nonwoven fabric, needlepunched nonwoven fabric, and air-through nonwoven fabric can be used. Raw material fibers which can constitute the nonwoven fabric include olefin (such as polyethylene or polypropylene)-, polyester-, and polyamide-based synthetic fibers, as well as regenerated fibers such as rayon and cupra, and natural fibers such as cotton.

As shown in FIGS. 1 and 2, the first elastic members 61 are disposed in the vicinities of the inner edges of the pair of side sheets 5, respectively. More specifically, as shown in FIGS. 2 and 3, the first elastic members 61 are interposed between the side sheets 5 folded back at the inner edge sides, and are fixed in a stretched state to the side sheets 5.

The first elastic members 61 are disposed across the back portion A through the abdominal portion C of the pet diaper 1.

As shown in FIGS. 1 to 3, the second elastic members 62 are disposed in a pair of side portions, respectively, along the longitudinal direction LD of the pet diaper 1. More specifically, as shown in FIGS. 2 and 3, the second elastic members 62 are disposed between the side sheet 5 and the back sheet 31. The second elastic members 62 are fixed in the stretched state to the side sheets 5 and the back sheet 31.

The second elastic members 62 are disposed in the entire area of the crotch portion B, and a part of the back portion A and the abdominal portion C, of the pet diaper 1.

The pair of fastening tapes 7 is disposed in both sides of the abdominal portion C in the width direction WD of the pet diaper 1. More specifically, the pair of fastening tapes 7 are attached to portions of the abdominal portion C, in which the side sheets 5 and the back sheet 31 extend outwardly in the width direction WD, and the pair of fastening tapes 7 extend outwardly in the width direction from both side portions of the abdominal portion C. A plurality of hook members (not shown) are provided on one surface of the fastening tape 7.

As shown in FIG. 1, the landing tape 8 is disposed on an outer face of the back portion A (a surface on the back sheet 31 side). The landing tape 8 is configured in a rectangular shape, and is attached such that the longitudinal direction thereof coincides with the width direction WD of the pet diaper 1. A plurality of loop members (not shown) are provided on an outer surface of the landing tape 8, and the hook members of the fastening tape 7 are engaged with the loop members, thereby latching the fastening tapes 7 to the landing tape 8.

Next, the tail through-hole portion 100 of the first embodiment is described with reference to FIG. 4. FIG. 4 is an enlarged plan view showing the tail through-hole portion 100 according to the first embodiment.

As shown in FIG. 4, the tail through-hole portion 100 is formed in a region where the core wrapping sheet 42 is disposed in the central portion of the back portion A in the width direction WD. The tail through-hole portion 100 includes a first cut portion 110, a second cut portion 120, and a pair of first easily-incised portions 130.

As shown in FIGS. 1 and 4, the first cut portion 110 is formed in curved arcuate (semicircular) shape as a convex toward the end portion on the back portion A side of the pet diaper 1 in the longitudinal direction LD (a side opposite to the crotch portion B side). As shown in FIGS. 3 and 4, the first cut portion 110 includes: two incised portions 111 formed by incising the members constituting the back portion A (the surface sheet 2, the two core wrapping sheets 42, the waterproof sheet 32, and the back sheet 31); and a non-incised portion 112 provided between the two incised portions 111.

The two incised portions 111 are formed in line-symmetric shape with respect to a longitudinal central line CL extending in the longitudinal direction LD of the pet diaper 1 (see FIG. 4). The non-incised portion 112 is configured in length enabling easy separation thereof (for example, approximately 3 mm).

In the first cut portion 110, the two incised portions 111 are connected by separating the non-incised portion 112. As a result, the first cut portion 110 forms the arcuate (semicircular) tail through-hole.

The second cut portion 120 is disposed closer to the crotch portion B side than the first cut portion 110. More specifically, as shown in FIG. 1, the second cut portion 120 is disposed in the back portion A in the vicinity of the border with the crotch portion B, in proximity to the absorbent core 41. Similarly to the first cut portion 110, the second cut portion 120 is formed in curved arcuate (semicircular) shape as a convex toward the end portion on the back portion A side of the pet diaper 1 in the longitudinal direction LD. The second cut portion 120 includes: two incised portions 121 formed by incising the members constituting the back portion A (the surface sheet 2, the two core wrapping sheets 42, the waterproof sheet 32, and the back sheet 31); and a non-incised portion 122 provided between the two incised portions 121.

The two incised portions 121 are formed in line-symmetric shape with respect to the longitudinal central line CL extending in the longitudinal direction LD of the pet diaper 1. The non-incised portion 122 is configured in length enabling easy separation thereof (for example, approximately 3 mm).

In the second cut portion 120, the two incised portions 121 are connected by separating the non-incised portion 122. As a result, the second cut portion 120 forms the arcuate (semicircular) tail through-hole.

As shown in FIG. 4, the pair of first easily-incised portions 130 extends from the second cut portion 120 toward the first cut portion 110. More specifically, the pair of first easily-incised portions 130 is formed to connect the end portion of the first cut portion 110 on the crotch portion B side with the side portions of the second cut portion 120 in the width direction WD.

In the first embodiment, the pair of first easily-incised portions 130 is configured by perforations formed in the back portion A. A length L1 of each perforation (a length of each incision) is configured to be shorter than a length of the incised portion 111 constituting the first cut portion 110, and shorter than a length of the incised portion 121 constituting the second cut portion 120. The length L1 of each perforation is configured to be shorter than a length L2 of each non-incision in the perforations. More specifically, the length L1 of each perforation is formed to be 3 to 5 mm, and the length L2 of each non-incision is formed to be 4 to 6 mm.

In the tail through-hole portion 100, a width W1 of the first cut portion 110 in the width direction WD is preferably 20 to 50 mm. A length L3 of the first cut portion 110 in the longitudinal direction LD is preferably 20 to 50 mm.

A width W2 of the second cut portion 120 in the width direction WD is preferably 20 to 50 mm. A length L4 of the second cut portion 120 in the longitudinal direction LD is preferably 20 to 50 mm.

A length L5 between the first cut portion 110 and the second cut portion 120 is preferably 15 to 40 mm.

In the pet diaper 1, the first elastic members 61 are fixed in the stretched state to the pair of side sheets 5, respectively, along the longitudinal direction LD of the pet diaper 1. The second elastic members 62 are fixed in the stretched state to both sides of the crotch portion B, respectively, along the longitudinal direction LD of the pet diaper 1. Therefore, when the pet diaper 1 is in a natural state (a state where no external force is applied), a pair of leg gather portions 11 stretchable in the longitudinal direction LD is formed in the pair of side portions of the pet diaper 1, respectively, along the longitudinal direction LD (see FIGS. 5 and 6). The free end sides of the pair of side sheets 5 stand up to form pocket portions 12, respectively, between inner faces of the side sheets 5 and an outer face of the surface sheet 2 (see FIG. 2).

Figure 5:
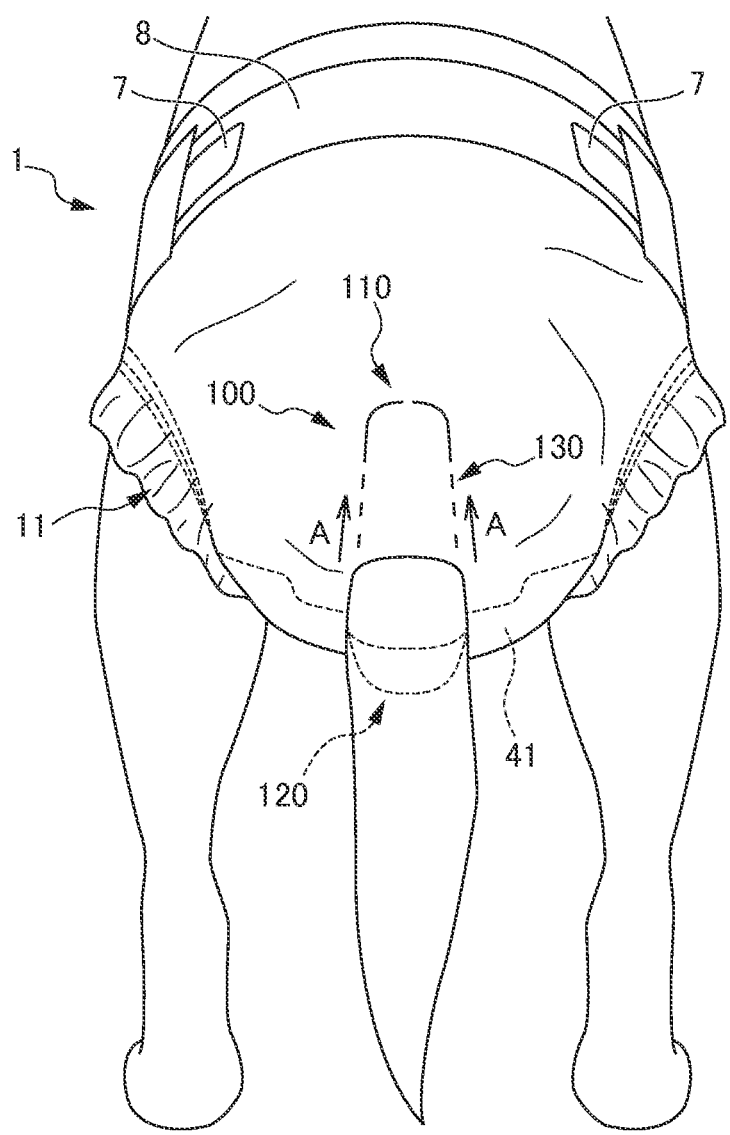
FIG. 5 is a diagram showing a state where the pet diaper of the first embodiment is put on a female pet.
Figure 6:
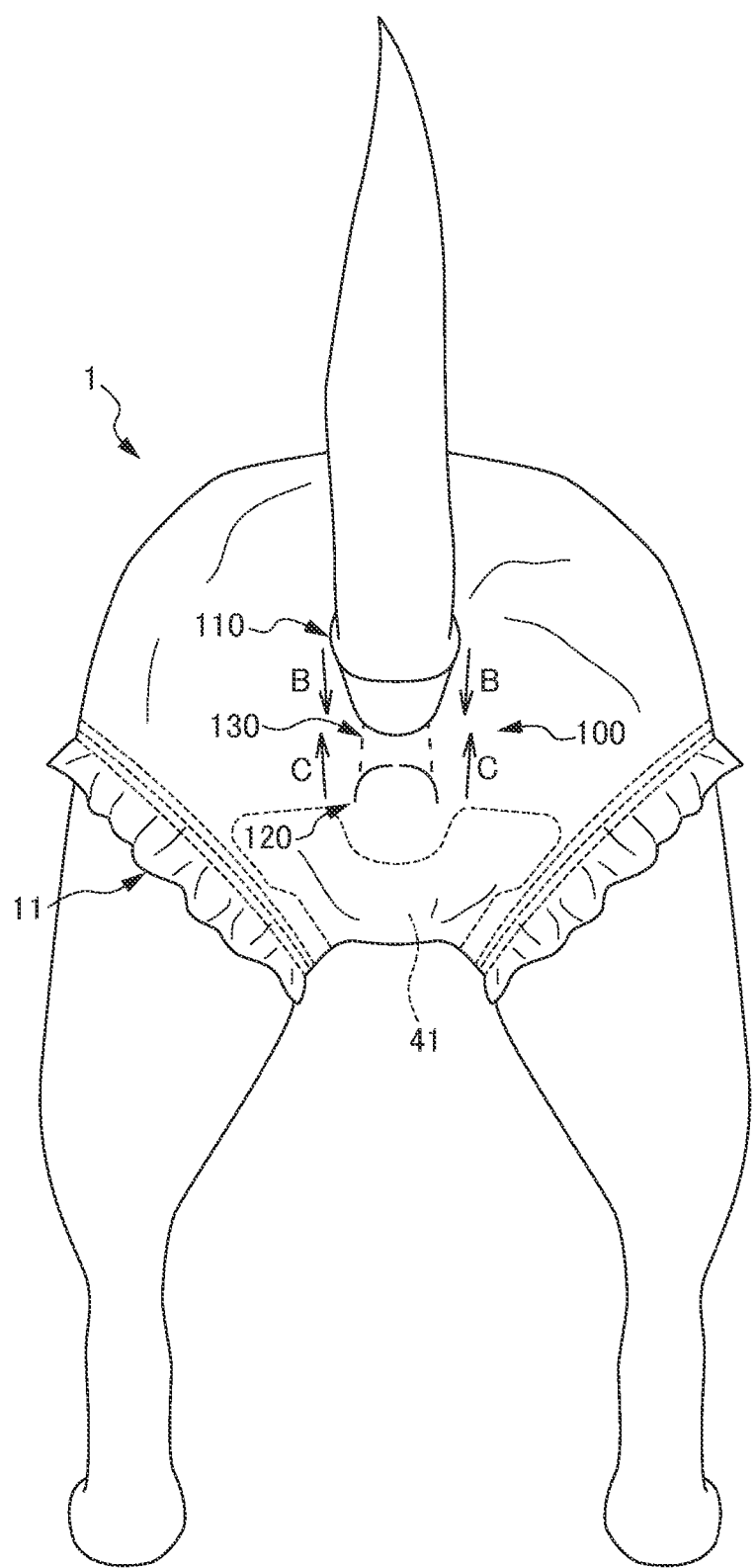
FIG. 6 is a diagram showing a state where the pet diaper of the first embodiment is put on a male pet.

Next, with reference to FIGS. 5 and 6, descriptions are provided for a state where the pet diaper 1 of the first embodiment is put on a pet. FIG. 5 is a diagram showing a state where the pet diaper 1 of the first embodiment is put on a female dog as a pet. FIG. 6 is a diagram showing a state where the pet diaper 1 of the first embodiment is put on a male dog as a pet.

First of all, with reference to FIG. 5, descriptions are provided for a case in which the pet diaper 1 is put on a female dog as a pet.

A urethral opening of a female dog is located between bases of hind legs. Therefore, in order for the absorbent 4 (the absorbent core 41) to preferably absorb urine excreted from a part between the bases of the hind legs, it is preferable for the crotch portion B including the absorbent core 41 to be positioned posteriorly to the body of the dog (to the vicinity of the tail) as much as possible.

Accordingly, in a case in which the pet diaper 1 is put on a female dog, the non-incised portion 122 of the second cut portion 120 is firstly separated to form a tail through-hole in the second cut portion 120, and the tail of the dog is passed through the tail through-hole. Subsequently, while the back portion A is placed on a posterior part of the back of the dog, the abdominal portion C is pushed forward to a ventral part from between the hind legs of the dog. Subsequently, both sides of the abdominal portion C are pulled up to the back side along the waist of the dog, and the pair of fastening tapes 7 disposed on the abdominal portion C are engaged with the landing tape 8 disposed on the outer surface of the back portion A.

As a result, as shown in FIG. 5, the pet diaper 1 can be put on a dog in a state where the absorbent core 41 is positioned posteriorly to the vicinity of the tail. In a case in which the tail of the diaper-wearing dog is thick, a tail through-hole of preferred size can be formed by incising the first easily-incised portions 130 toward the first cut portion 110 side (see an arrow A in FIG. 5).

Next, with reference to FIG. 6, descriptions are provided for a case in which the pet diaper 1 is put on a male dog.

A urethral opening of a male dog is located on a genital tip anterior to bases of hind legs. Therefore, in a case in which the pet diaper 1 is put on a male dog as a pet, in order to preferably absorb urine excreted from the part anterior to the bases of the hind legs, it is preferable for the abdominal portion C including the absorbent 4 (absorbent core 41) to be in a position anterior to the body as much as possible.

Accordingly, in a case in which the pet diaper 1 is put on a male dog, the non-incised portion 112 of the first cut portion 110 is separated to form a tail through-hole in the first cut portion 110 at first, and the tail of the dog is then passed through the tail through-hole. Subsequently, while the back portion A is placed on a posterior part of the back of the dog, the abdominal portion C is pushed forward to a ventral part from between the hind legs of the dog. Subsequently, both sides of the abdominal portion C are pulled up to the back side along the waist of the dog, and the pair of fastening tapes 7 disposed on the abdominal portion C are engaged with the landing tape 8 disposed on the outer surface of the back portion A.

In this way, by passing the tail through the first cut portion 110 provided on the end portion side of the back portion A, as shown in FIG. 6, the pet diaper 1 can be put on a dog in a state where the abdominal portion C (absorbent core 41) is positioned anteriorly to the body of the dog, as compared to the state shown in FIG. 5. As a result, in a case in which the pet diaper 1 is fitted, the abdominal portion C can preferably cover an area including the genital tip side; therefore, leakage of urine from the abdominal portion C side can be reduced. In a case in which the tail of the diaper-wearing dog is thick, a tail through-hole of preferred size can be formed by incising the first easily-incised portions 130 toward the second cut portion 120 side (see an arrow B in FIG. 6).

Furthermore, in this case, the anus of the dog is located in the vicinity of the position where the second cut portion 120 is formed. Therefore, in a case in which feces are not desired to be excreted inside the pet diaper 1 in a state where the pet diaper 1 is put on a dog, by opening the second cut portion 120 by separating the non-incised portion 122 of the second cut portion 120, feces can be excreted to the outside of the pet diaper 1 in a state where the pet diaper 1 is put on a dog. In a case in which an opening for excreting feces is small, an opening of preferred size can be formed by incising the first easily-incised portions 130 toward the first cut portion 110 side (see an arrow B in FIG. 6). As a result, feces can be excreted to the outside of the pet diaper 1 without opening the tail through-hole larger than necessary, formed in the first cut portion 110.

According to the pet diaper 1 of the first embodiment described above, the following function and effects are achieved.

(1) A urethral opening of a female dog is located between bases of hind legs, whereas a urethral opening of a male dog is located on a genital tip anterior to bases of hind legs. Accordingly, the tail through-hole portion 100 is configured to include: the first cut portion 110 provided to the back portion A; and the second cut portion 120 provided to the back portion A more closely to the crotch portion B side than the first cut portion 110. As a result, in a case in which the pet diaper 1 is put on a female dog, a tail through-hole can be formed in the second cut portion 120 located in the crotch portion B side; and in a case in which the pet diaper 1 is put on a male dog, a tail through-hole can be formed in the first cut portion 110. Therefore, in a case in which the pet diaper 1 is put on a female dog, the crotch portion B including the absorbent core 41 is located in the vicinity of the tail; and in a case in which the pet diaper 1 is put on a male pet, the abdominal portion C including the absorbent core 41 is located anteriorly to the body of the pet; therefore, the pet diaper 1 can be fitted in an appropriate position in accordance with the gender of the pet.

(2) The tail through-hole portion 100 is configured to include the pair of first easily-incised portions 130 extending from the second cut portion 120 toward the first cut portion 110. As a result, in a case in which the pet diaper 1 is put on a female dog, a tail through-hole of preferred size can be formed by appropriately incising the first easily-incised portions 130 from the second cut portion 120 side toward the first cut portion 110 side. Therefore, a tail through-hole of preferred size can be formed while reducing the size of the second cut portion 120. Since the tail through-hole is not extended to the crotch portion B side surpassing the second cut portion 120, the second cut portion 120 can be disposed more closely to the absorbent core 41. As a result, leakage of urine or the like from the second cut portion 120 can be reduced. In a case in which the pet diaper 1 is put on a male dog, a tail through-hole of preferred size can be formed by appropriately incising the first easily-incised portions 130 from the first cut portion 110 side toward the second cut portion 120 side.

Furthermore, in a case in which the pet diaper 1 is put on a male dog, the anus of the dog is located in the vicinity of the position where the second cut portion 120 is formed. Therefore, in a case in which feces are not desired to be excreted inside the pet diaper 1 in a state where the pet diaper 1 is put on a dog, by opening the second cut portion 120 by separating the non-incised portion 122 of the second cut portion 120, feces can be excreted to the outside of the pet diaper 1 in a state where the pet diaper 1 is put on a dog. In a case in which an opening for excreting feces is small, an opening of preferred size can be formed by incising the first easily-incised portions 130 toward the first cut portion 110 side (see an arrow B in FIG. 6). As a result, feces can be excreted to the outside of the pet diaper 1 without opening the tail through-hole larger than necessary, formed in the first cut portion 110.

(3) The first cut portion 110 is configured to include the two incised portions 111 and the non-incised portion 112; and the second cut portion 120 is configured to include the two incised portions 121 and non-incised portion 122. As a result, the non-incised portions 112 and 122 can prevent an unnecessary opening of the first cut portion 110 and the second cut portion 120. Therefore, it is possible to prevent adverse effects due to opening the first cut portion 110 and the second cut portion 120 when not in use for a tail through-hole or the like.

For example, in a case in which the pet diaper 1 is put on a male dog, the anus of the dog is located in the vicinity of the position where the second cut portion 120 is formed. In this regard, the non-incised portion 122 maintains the second cut portion 120 in a closed state. As a result, even in a case in which a male dog wearing the pet diaper 1 excretes feces, the excreted feces can be prevented from escaping from the second cut portion 120.

(4) The first easily-incised portions 130 are configured by perforations, in which the lengths of the incised portions 111 and 121 are longer than the length L1 of the perforations. As a result, the positions of the first cut portion 110 and the second cut portion 120 can be more easily visually observed than the first easily-incised portions 130; and the first cut portion 110 and the second cut portion 120 can be more easily opened than the first easily-incised portions 130. Therefore, an owner who puts the pet diaper 1 on a dog can easily recognize the positions of the first cut portion 110 and the second cut portion 120; and the pet diaper 1 can be fitted in an appropriate position in accordance with the gender of the pet.

(5) The absorbent body is configured to include the absorbent core 41 and the core wrapping sheet 42 that wraps the absorbent core 41; and the core wrapping sheet 42 is also disposed in the back portion A. As a result, the core wrapping sheet 42 is disposed in the position where the first cut portion 110 and the second cut portion 120 are formed. Therefore, since the core wrapping sheet 42 can absorb liquid such as urine leaked from the first cut portion 110 and the second cut portion 120, leakage of liquid from the tail through-hole portion 100 can be reduced more effectively.

Figure 7:
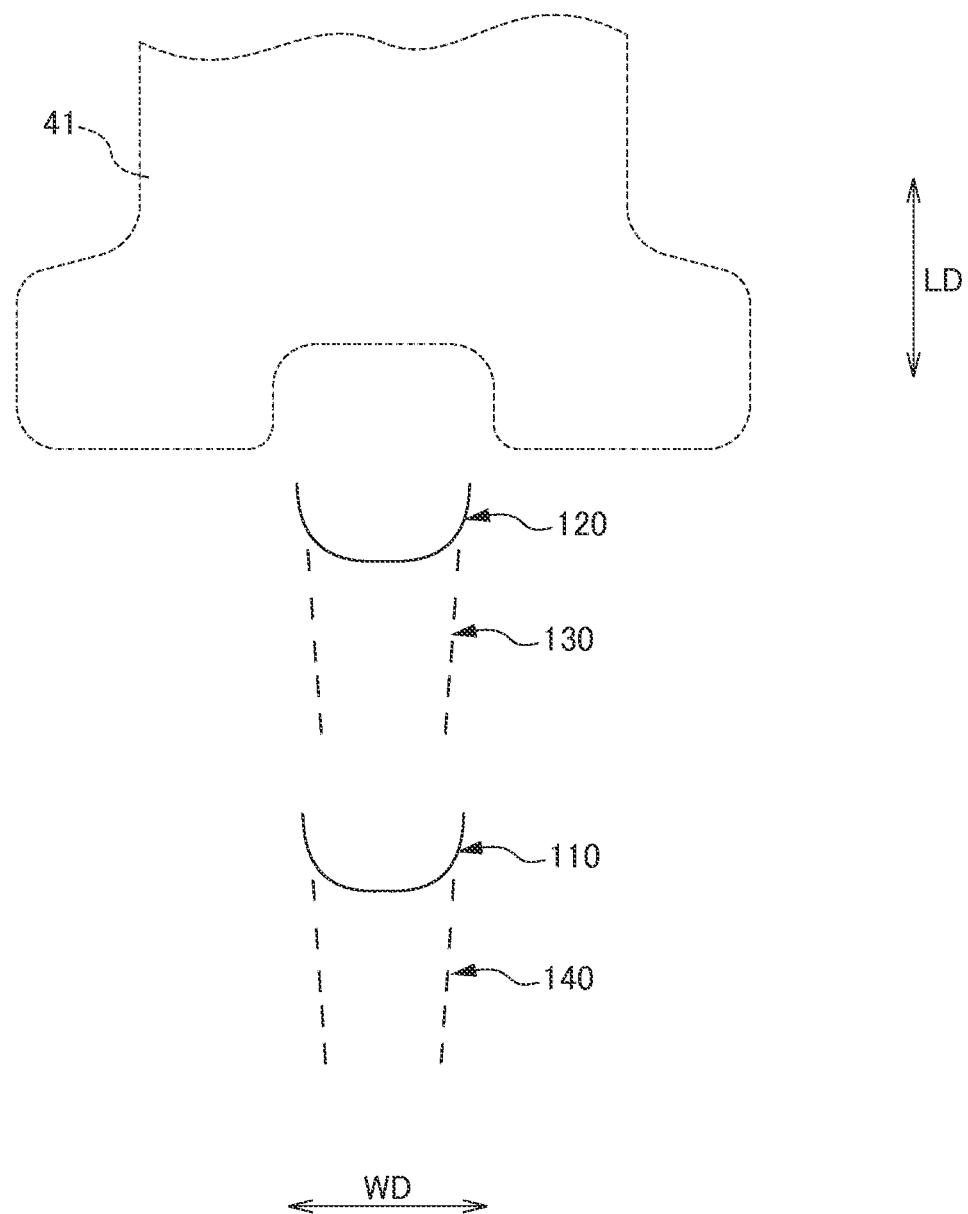
FIG. 7 is a plan view showing a vicinity of a tail through-hole portion of a pet diaper of a second embodiment.

Next, a pet diaper 1 according to a second embodiment of the present invention is described with reference to FIG. 7. FIG. 7 is a plan view showing the pet diaper 1 of the second embodiment.

In the following descriptions of the second embodiment, the same components are denoted with the same reference numerals, and descriptions thereof will be omitted or simplified.

The pet diaper 1 of the second embodiment differs from the pet diaper 1 of the first embodiment in configuration of the tail through-hole portion 100.

In the second embodiment, a tail through-hole portion 100 further includes a pair of second easily-incised portions 140.

As shown in FIG. 7, the pair of second easily-incised portions 140 extends from sides of a first cut portion 110 in a width direction WD toward an end of a back portion A.

The pair of second easily-incised portions 140 is configured by perforations formed in the back portion A. A length of each perforation is configured to the same as the length of each perforation constituting the first easily-incised portions 130.

In the second embodiment, the first cut portion 110 and the second cut portion 120 are configured without including a non-incised portion.

The pet diaper 1 according to the second embodiment achieves the following effects, in addition to the abovementioned effects (1), (2), (4) and (5).

(6) The tail through-hole portion 100 is configured to include the pair of second easily-incised portions 140. As a result, the size of the tail through-hole formed in the first cut portion 110 can be preferably adjusted by incising the second easily-incised portions 140.

The preferred embodiments of the present invention have been described above; however, the present invention is not limited thereto and can be appropriately changed.

For example, in the first and second embodiments, the present invention is applied to a development type of the pet diaper 1 that is put on by using the pair of fastening tapes 7 and the landing tape 8; however, the present invention is not limited thereto. In other words, the present invention may be applied to a so-called pull-up (underpants) type of pet diaper.

In the first embodiment, the first cut portion 110 is configured by the two incised portions 111 and the non-incised portion 112 provided between the two incised portions 111; and the second cut portion 120 is configured by the two incised portions 121 and the non-incised portion 122 provided between the two incised portions 121; however, the present invention is not limited thereto. In other words, the first cut portion and the second cut portion may be configured by at least three incised portions and at least two non-incised portions.

Figure 8:
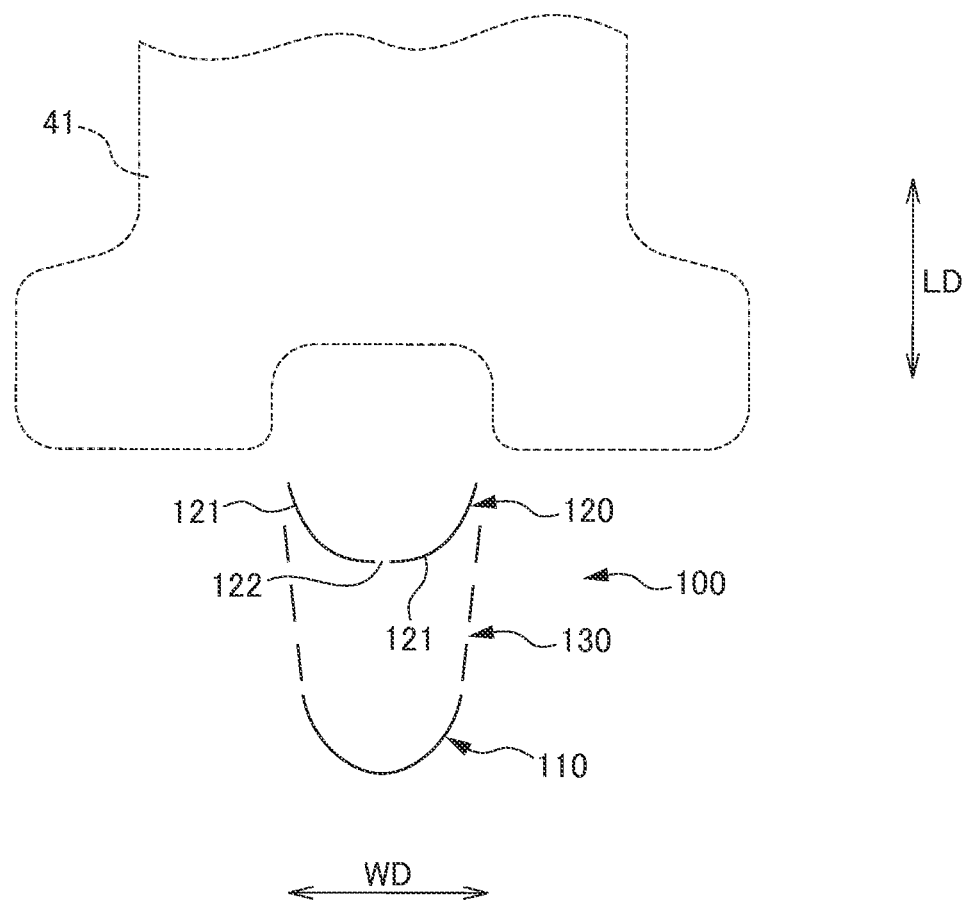
FIG. 8 is a plan view showing a modification example of the tail through-hole portion.

As shown in FIG. 8, only the second cut portion 120 may be configured by two incised portions 121 and a non-incised portion 122 provided between the two incised portions 121; and the first cut portion 110 may be configured without providing a non-incised portion.

Figure 9:
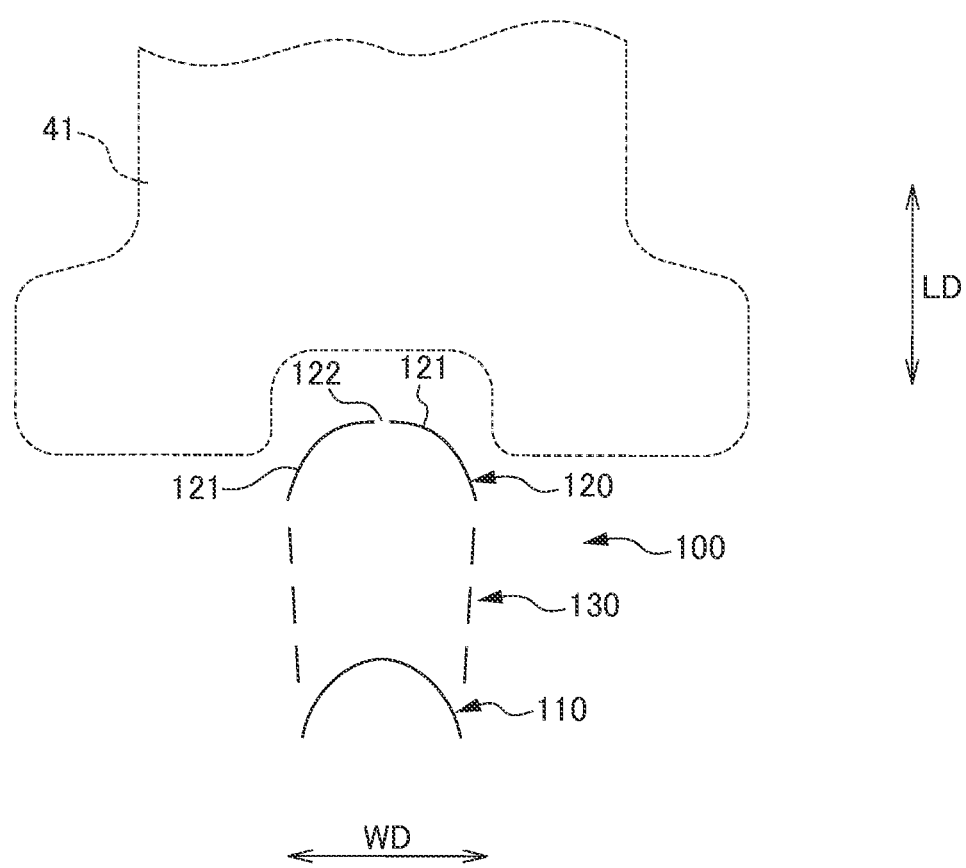
FIG. 9 is a plan view showing a modification example of the tail through-hole portion.

In the first and second embodiments, the first cut portion 110 and the second cut portion 120 are formed as a convex toward the end portion on the back portion A side of the pet diaper 1 in the longitudinal direction LD (a side opposite to the crotch portion B side); however, the present invention is not limited thereto. In other words, as shown in FIG. 9, the first cut portion 110 and the second cut portion 120 may be formed as a convex toward the crotch portion B side.

In the first and second embodiments, the first easily-incised portions 130 and the second easily-incised portions 140 are configured by perforation; however, the present invention is not limited thereto. In other words, the first easily-incised portions and the second easily-incised portions may be configured such that only some of the members configuring the back portion A (for example, a surface sheet, a waterproof sheet, and a back sheet) are incised for the entire length of the first easily-incised portions and the second easily-incised portions, and the other members (for example, a core wrapping sheet) are not incised.

The invention claimed is:

1. A diaper for a pet, said diaper comprising:
a liquid permeable surface layer;
a liquid impermeable back layer;
a liquid absorbent layer disposed between the surface layer and the back layer;
a back portion configured to be disposed in a vicinity of a back of the pet;
an abdominal portion configured to be disposed in a vicinity of an abdomen of the pet;
a crotch portion configured to be disposed in a vicinity of a crotch of the pet, the crotch portion disposed between the back portion and the abdominal portion in a longitudinal direction of the diaper;
a first cut portion provided in the back portion, and being convex away from the crotch portion or being convex toward the crotch portion, the first cut portion includes a plurality of first incised portions penetrating through the surface layer and the back layer;
a second cut portion provided closer to the crotch portion than the first cut portion, disposed separately from the first cut portion, and being convex away from the crotch portion or being convex toward the crotch portion, the second cut portion includes a plurality of second incised portions penetrating through the surface layer and the back layer; and
a first easily-incised portion extending from the second cut portion toward the first cut portion,
wherein the liquid absorbent layer extends from the abdominal portion to a border between the crotch portion and the back portion in the longitudinal direction without being disposed in the back portion and terminates at a position before the second cut portion.

2. The diaper according to claim 1, wherein
at least one of the first cut portion or the second cut portion includes a non-incised portion provided between two incised portions that are adjacent to each other among the first incised portions or among the second incised portions.

3. The diaper according to claim 2, wherein the first easily-incised portion includes perforations, and
wherein a length of each of the first and second incised portions is longer than a length of each of the perforations.

4. The diaper according to claim 3, wherein the length of each of the perforations is shorter than a distance between adjacent perforations.

5. The diaper according to claim 1, further comprising a second easily-incised portion extending from the first cut portion to an end side of the back portion.

6. The diaper according to claim 1,
wherein the absorbent layer includes a liquid absorbent core and a core wrapping sheet wrapping the absorbent core,
wherein the absorbent core is disposed in the abdominal portion and the crotch portion but not in the back portion, and
wherein the core wrapping sheet is disposed in the abdominal portion, the crotch portion and the back portion.

7. The diaper according to claim 6, wherein the first and second cut portions extend through the core wrapping sheet, but not the absorbent core, in a thickness direction of the diaper.

8. The diaper according to claim 6, wherein an entirety of the absorbent core is located, in the longitudinal direction, on one side of the second cut portion.

9. The diaper according to claim 1, wherein
each of the first and second cut portions has two ends opposing each other in a width direction perpendicular to the longitudinal direction, and
a distance between the two ends of the first cut portion in the width direction is less than a distance between the two ends of the second cut portion in the width direction.

10. The diaper according to claim 1, wherein the first and second cut portions are both convex toward the crotch portion.

11. The diaper according to claim 1, wherein the first and second cut portions are both convex away from the crotch portion.

12. The diaper according to claim 1, wherein the first cut portion is not continuous with the second cut portion.

13. The diaper according to claim 1, wherein
the first and second cut portions are both convex away from the crotch portion,
each of the first and second cut portions has two ends opposing each other in a width direction perpendicular to the longitudinal direction, and
a distance between the two ends of the first cut portion in the width direction is less than a distance between the two ends of the second cut portion in the width direction.

14. The diaper according to claim 13, wherein
the first cut portion further includes a first non-incised portion between two of the first incised portions that are adjacent to each other, and
the second cut portion further includes a second non-incised portion provided between two of the second incised portions that are adjacent to each other.

15. A diaper for a pet, said diaper comprising:
a liquid permeable surface layer;
a liquid impermeable back layer;
a liquid absorbent layer disposed between the surface layer and the back layer;
a back portion configured to be disposed in a vicinity of a back of the pet;
an abdominal portion configured to be disposed in a vicinity of an abdomen of the pet;
a crotch portion configured to be disposed in a vicinity of a crotch of the pet, the crotch portion disposed between the back portion and the abdominal portion in a longitudinal direction of the diaper;
a first cut portion provided in the back portion, and being convex away from the crotch portion or being convex toward the crotch portion, the first cut portion includes a single first incised portion penetrating through the surface layer and the back layer;
a second cut portion provided closer to the crotch portion than the first cut portion, disposed separately from the first cut portion, and being convex away from the crotch portion or being convex toward the crotch portion, the second cut portion includes a plurality of second incised portions penetrating through the surface layer and the back layer; and
a first easily-incised portion extending from the second cut portion toward the first cut portion,
wherein
the liquid absorbent layer extends from the abdominal portion to a border between the crotch portion and the back portion in the longitudinal direction without being disposed in the back portion and terminates at a position before the second cut portion, the first cut portion includes the single first incised portion without a non-incised portion, and the second cut portion includes a non-incised portion provided between two of the second incised portions that are adjacent to each other.

* * * * *